United States Patent [19]

Cremonesi

[11] 4,292,409

[45] Sep. 29, 1981

[54] FLOW REACTOR FOR ENZYMATIC REACTIONS IN WHICH THE ENZYME IS IMMOBILIZED ON A SOLID MATRIX HAVING A PLANAR SURFACE

[75] Inventor: Pietro Cremonesi, Milan, Italy

[73] Assignee: Italfarmaco S.p.A., Milan, Italy

[21] Appl. No.: 79,036

[22] Filed: Sep. 26, 1979

[30] Foreign Application Priority Data

May 8, 1979 [IT] Italy ............................ 22448 A/79

[51] Int. Cl.³ ........................................... C12M 1/40
[52] U.S. Cl. ................................. 435/288; 435/310
[58] Field of Search ............... 435/288, 300, 301, 310

[56] References Cited

U.S. PATENT DOCUMENTS

| | | | |
|---|---|---|---|
| 3,769,175 | 10/1973 | Berdelle-Hilge | 435/288 |
| 3,859,050 | 1/1975 | Horn et al. | 435/288 |
| 3,884,641 | 5/1975 | Kraffczyk et al. | 435/288 |

Primary Examiner—Thomas G. Wyse
Attorney, Agent, or Firm—Bucknam and Archer

[57] ABSTRACT

A novel reactor for enzymatic reactions comprises a flow cell which is constituted by two semi-blocks having a planar surface. The enzyme is immobilized on one of the semi-blocks while a thin channel is provided on the face of the other semi-block. The two semi-blocks are hermetically closed. The substrate solution follows a tangential motion and travels with a laminar flow. The reactor permits to achieve 90% contact with the enzyme and may be used continuously.

6 Claims, 6 Drawing Figures

FLOW REACTOR FOR ENZYMATIC REACTIONS IN WHICH THE ENZYME IS IMMOBILIZED ON A SOLID MATRIX HAVING A PLANAR SURFACE

The present invention relates to a reactor suitable for carrying out enzymatic reactions. More specifically the invention relates to a flow reactor in which the enzymes being used are immobilized on a solid matrix having a planar surface.

It is well known that enzymes exhibit very high specificity with respect to the respective substrates. This specificity is the basis for the use of the enzymes for production as well as analytical purposes, in a variety of fields such as pollution control, production of foodstuff as well as clinical chemistry.

The limitations in the applicability of the enzymes are essentially due to two factors:
(a) The relative instability of the enzyme in an aqueous solution; and
(b) The cost of these enzymatic reactions, which is frequently very high, cost which could be considerably reduced if the enzyme could be reutilized, in a continuous or discontinuous fashion.

The well known principle of immobilization of enzymes on a solid matrix which is achieved by chemical reaction or by absorption minimizes the above-mentioned problems because it permits the recovery of the catalytic ability of the enzyme. From this principle and in view of the necessity of recovery of the catalytic activity of the enzyme in a continuous fashion, three methods have been developed, which methods are based on the use of continuous flow reactors with the enzymes being immobilized, for production as well as for analytical purposes. The three methods are based on the use of:
(1) A column with the enzyme being fixed on beads of suitable polymers
(2) A tube with the enzyme being fixed on the wall of the tube made of suitable material;
(3) A membrane with the enzyme being fixed on a suitable semi-permeable membrane or being immobilized within two semi-permeable membranes.

A common feature of every type of flow reactor is the contact between the enzyme which is immobilized and the substrate, and in some cases also the cofactors, which substrate is dissolved in a continuously flowing solution.

If one represents the contact between the substrate and the enzyme in terms of the length of time, this length of time becomes the principal, if not the only factor which influences the biochemical transformation of the substrate, also called the yield of the substrate conversion. For the purpose of achieving high substrate conversions, a process which frequently determines the signal to be used in the analytical determination of the substrate itself, it is advantageous that the period of contact between the enzyme and the substrate be the highest possible, as long as it is compatible with (1) the dimension characteristics as well as manufacturing requirements of the flow reactor and (2) total period of time involved in the analysis so that the enzymatic method on a routine scale is useful. This is intended to achieve such a yield of conversion that it is possible to obtain a sensibility of detection useful in analytical applications.

The continuous flow reactors which employ a thin tube have been found to be of valuable application for analytical purposes, in spite of the fact that they present substantial difficulties in the immobilization of the enzyme on the internal wall of the tube, which immobilization may be achieved only by chemical means and cannot be achieved by adsorption. Further this type of reactor involves volumes of liquid which are not negligible with substantial consumption of reagents.

Also the flow reactors which have columns packed with beads have been used but they present serious difficulties of mechanical resistance as a function of the flow, in addition to the problems of standardization of the flow when used in a continuous manner.

Further the production costs, although obviously varying from a model to another and varying from one enzyme to another enzyme, in general are quite high, particularly if one considers the fact that the life of the reactor depends on the period of activity of the enzyme being immobilized.

The crux of the present invention resides in providing a novel type of reactor for carrying out enzymatic reactions with the enzyme being immobilized on a matrix having a planar surface, which reactor overcomes the disadvantages mentioned hereinabove, which reactor presents the following advantages:
(1) The use of enzymes which are easily immobilized by chemical means on solid matrices as well as the use of enzymes which are more simply adsorbed on solid matrices;
(2) The use of reaction volumes which are as a whole very small;
(3) Laminar flow operation which is flat instead of being cylindrical with the resulting increase in contact between the enzyme and the substrate solution and in some cases also the cofactors;
(4) The use of supporting matrices which may be hydrophobic as well as proteinaceous in nature;
(5) The use of matrices of the type of filter paper which permit to achieve a flow reactor with properties very similar to the properties of reactors consisting of a packed column, with a substantial improvement of the flow characteristics;
(6) Elimination of the phenomena of diffusion which occur in reactors having a semi-permeable membrane during the enzymatic reaction, phenomena which are common, for instance in reactors having a membrane in a spiral arrangement or in reactors having the enzyme immobilized between two semi-permeable membranes. These phenomena of diffusion cause a remixing with the result that the actual concentration of the substrate in the reaction chamber decreases and also the rate of the enzymatic reaction decreases. The final result is a decrease of the yield of conversion and therefore a decrease of the intensity of the signal of detection of the enzymatic reaction itself;
(7) Reduction to a very minimum of the possibility of the materials mixing again after the enzymatic reaction has occurred; this remixing causes an appreciable decrease in sensitivity because it reduces the concentration of the product of the enzymatic reaction with resulting decrease in the intensity of the signal of detection;
(8) Ease of manufacture which is even more significant if one considers the substantial difficulties connected with other apparatuses particularly membrane reactors;
(9) Substantial reduction of production cost.

All these advantages are achieved without loss of the advantages of other types of reactors being commonly used because the simple replacement of the matrix having the enzyme immobilized on it, instead of replacing the entire reactor restores the operativeness of the reactor. The reactor according to the invention permits to combine the simplicity of the methods of immobilization of the enzyme on a surface, which may be accomplished in a stable manner by means of covalent bonds or more simply by adsorption, with the achievement of a laminar flow on the surface on which the enzyme is immobilized, which laminar flow is flat and presents a minimum thickness so that the possiblity of remixing which is typical with membrane reactors does not occur. Maximum contact efficiency between the two physical phases is achieved and therefore optimum catalytic effect is obtained in spite of a shorter contact time. These results are achieved by letting the solution follow a motion which must be tangential with respect to the surface, which is uniform and along any trajectory, for the purpose of causing contact between the fluid with the maximum amount of the supporting surface of the same enzymatic activity.

In the reactor according to the present invention this motion is achieved by means of a thin channel of any shape on one of the faces of a semi-block of a flow cell having two opposite faces, built of a chemical inert material for instance tetrafluoropolyethylene, polyvinyl chloride, polyethylene, polyamide, stainless steel, etc. while the other semi-block supports the immobilized enzyme. Alternatively this think channel mentioned hereinabove may be built in both semi-blocks. This channel may be obtained either directly by means of an incision on the surface of one or both blocks of the reactor or indirectly, for instance utilizing a lamina or a filament which may be of stainless steel or tetrafluoropolyethylene or of another inert material on which or by means of which the flow path is obtained, which channel is inserted between the two semi-blocks of the cell having a planar surface.

An essential requirement is that the walls between the two channels must be thin and smaller than the maximum dimensions of the flow channel. Apart from this requirement essentially the total amount of the enzyme supported on the solid matrix having a planar surface will be in contact with the solution of the substrate and will be therefore in condition suitable to perform catalytic activity.

The introduction and the exit of the circulating solution may be placed in any two points of each of the two semi-blocks, independently from the direction of circulation of the solution. In this manner the reactor results essentially constituted by a thin channel of various shapes.

Provided the laminar flow is as thin as possible, the enzymatic activity will be sufficient to achieve a good conversion rate of the substrate to the product with a consequent possibility of reducing the contact surfaces as well as consequently the volumes which have to be employed.

If it appears to be advantageous to subject the same substrate to a series of two or more successive reactions, it is possible to build the reactor according to the present invention in the shape of a modular reactor containing two or more reaction chambers in accordance with this invention as described hereinabove, separated one from the other by means of semi-blocks of suitable shape and connected among themselves by means of orifices of such shape that the solution containing the substrate may go through successively the same chambers.

By way of illustration of the present invention an example of a flow micro reactor having the enzyme immobilized on solid matrices having a planar surface and two examples of application of the same reactor are described hereinbelow. The invention is further illustrated by the accompanying figures of which:

EXAMPLE 1

Construction and assembly of a flow micro-reactor

Figure 1:
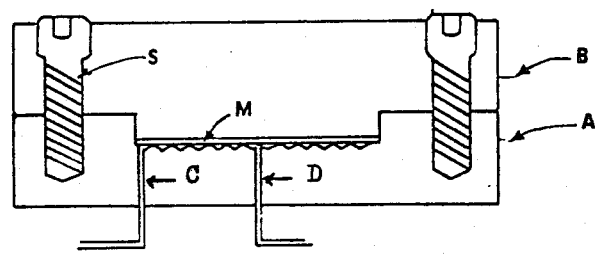
FIG. 1 is a schematic representation in transversal section of a flow micro reactor.

By reference to FIG. 1 the letter A designates one of the semi-blocks which is made for instance of plastic material, such as the material commercially available under the name Sicodur. On this semi-block a thin continuous channel is obtained by incision which in this specific case has the shape of a spiral. In this case the channel has a triangular cross section, maximum depth of 0.5 mm with a bse of 1 mm, length of 180 mm and a volume of 45 $\mu$l.

The enzyme is immobilized on a solid matrix M having planar surface, in the shape of a sheet or film, for instance in the particular example a filter paper. It should be noted, however, that any other material, both hydrophobic of hydrophilic, in the shape of a sheet or a film or a membrane may be used. The sheet or film is caused to adhere to the semi-block B which is so constructed that the cellulose matrix is compressed against the spirals of the semi-block A. In the specific example illustated in the figure the two semi-blocks are hermetically closed by means of fastening screws, S.

The means for the inlet and outlet of the solution are provided in the same semi-block A by means of orifices of suitable dimensions, for instance 0.2 mm $\phi$ (diameter) which are designated by the letters C and D in FIG. 1 for the purpose of avoiding the occurrence of remixing. Pipe fittings of suitable material, for instance a polyamide or tetrofluoropolyethylene or steel are mounted on these orifices, the orifices having analogous diameter, 0.2 mm. The pipe fittings are respectively connected with a system for the introduction of the fluid and also a system for the detection of the signal of the enzymatic reaction. In the specific example a spectroscopic detector is used but it is possible to use detectors of electrochemical or spectrofluorimetric or others.

Figure 2:
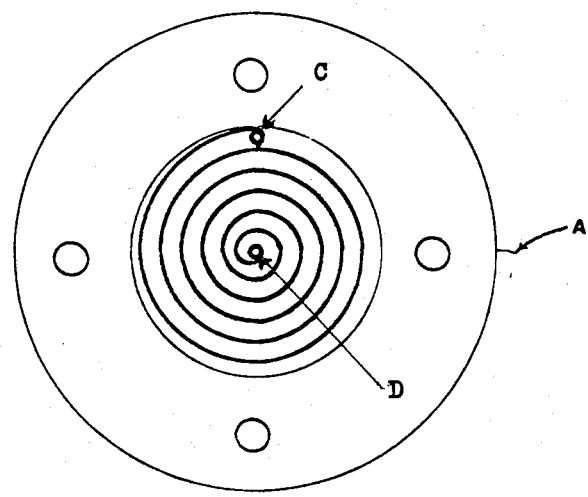
FIG. 2 is a top view of the semi-block A of FIG. 1.
Figure 3:
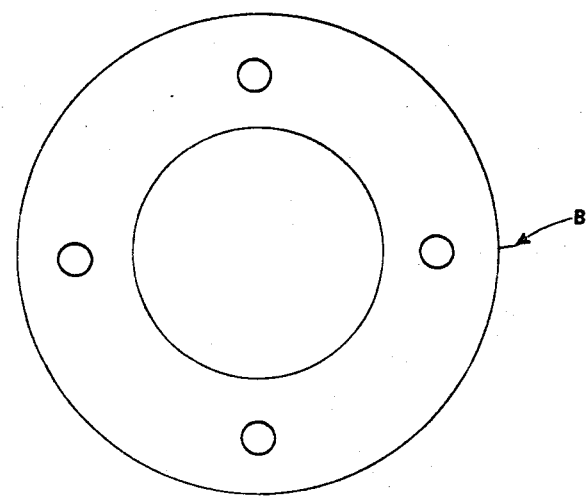
FIG. 3 is a top view of semi-block B.

As shown in FIG. 2, the semi-block A of FIG. 1 is provided with openings C and D for the inlet and the outlet respectively.

In the reactor which is illustrated in this example the percentage of active surface of the enzyme coming in contact with the solution with respect to the total amount of solution is 90%.

With this apparatus the enzyme is immobilized but it is easy to substitute one enzyme with another enzyme either because the first enzyme is exhausted or because it is desired to operate with an enzyme having different activity. The substitution is simply carried out by substitution of the matrix while the entire reactor is being used again. This constitutes a substantial difference between the reactor of the present invention and other flow reactors having enzymatic activity which require a complete substitution when the enzymatic activity is substantially decreased.

EXAMPLE 2

"Application of the micro-reactor with a discontinuous introduction of the substrate."

Figure 4:
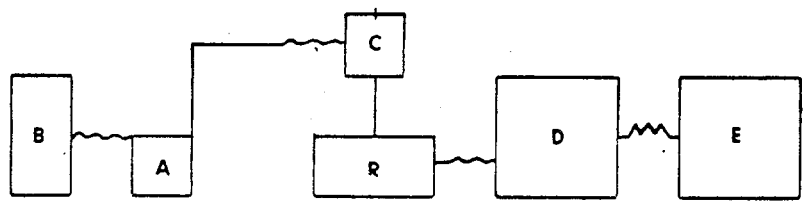
FIG. 4 illustrates schematically the flow micro-reactor described in Example 1 which is mounted in line on the apparatus.

The flow micro-reactor described in Example 1 is mounted in line in the entire apparatus schematically shown in FIG. 4. The letter A designates a pump having variable delivery. The letter B designates the reservoir of the buffer solution. The letter C is an injector having a septum, the letter R designates the flow reactor. The detector of spectrophotometric type is designated by the letter D and the letter E designates a system of registering the signal emanated by the detector D.

In actual operation a suitable buffer solution is caused to flow, for instance at a flow rate of 0.25 ml/minute, through the reactor in which is mounted a film or a sheet or a membrane having enzymatic activity, for instance peroxidase. The enzyme is immobilized by means of covalent bonds or may be adsorbed on the matrix.

As soon as conditions of constant flow are obtained, an appropriate amount of the substrate solution is injected in the flow by means of the injector having a septum designated by the letter C. While traveling with a laminar flow through the thin channel which is formed in the reactor, the substrate is transormed under the action of the enzyme. This transformation produces in the detection system D a variation of the signal which is registered in E.

Figure 5:
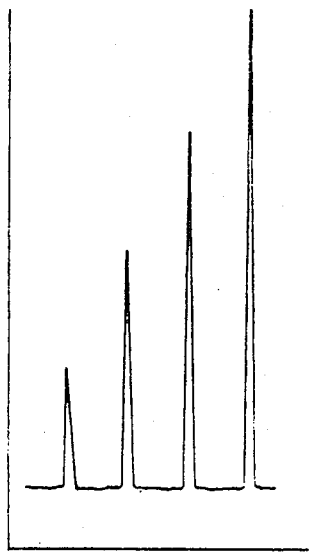
FIGS. 5 and 6 illustrate output signals from the reactor.

As shown in FIG. 5 the signals being registered are proportional to the quantity of the substrate being introduced.

EXAMPLE 3

Application of the micro-reactor to a continuous introduction of the substrate, that is "steady state"

Example 2 described hereinabove covers an application of the flow reactor to the case in which small quantities of substrate are involved. When it is necessary to analyze solutions having a low concentration of substrate, it is possible to utilize the same apparatus for the substrate in a continuous manner by means of a suitable six-way valve, for instance of the loop type, which valve is charged with the substrate solution to be subjected to the enzymatic reaction.

Figure 6:
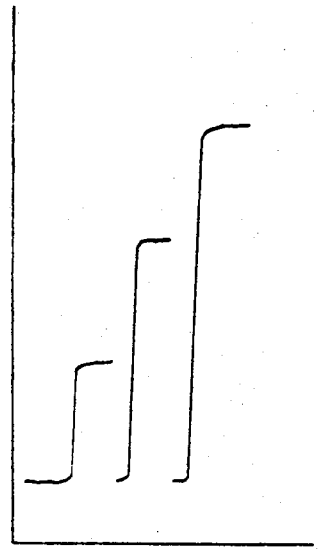

The same assembly illustrated in FIG. 4 is used with the only change that the injection system having a septum, designated by the letter C is substituted by an injection system having a valve. Under the conditions of constant flow, a suitable amount of the solution of the substrate is introduced by means of the valve, the substrate undergoes the enzymatic reaction under conditions of stationary state. The enzymatic reaction produces in the system of detection D a variation of the signal which is registered on E. As shown in FIG. 6 the registered signal is proportional to the quantity of substrate present in the flowing solution.

What is claimed is:

1. A laminar flow reactor for reactions with an enzyme or a cofactor in which the enzyme or cofactor is immobilized on a matrix having planar surface, and the reaction solution is continuously introduced to react with said enzyme or said cofactor which consists of a cell comprising two semi-blocks having a planar surface, the first of said semi-blocks being provided with a spiral channel, said channel constituting the reaction chamber having a laminar flow, said two semi-blocks being hermetically fastened, the second semi-block closes said reaction chamber, said matrix adhering onto said second semi-block, and being compressed against said channel, and wherein one orifice is provided at the inlet of the spiral and one orifice is provided at the outlet of the spiral, said reaction solution being introduced through the inlet flowing through said channel with a laminar flow and being removed from the outlet after it has come in contact with said matrix.

2. The reactor according to claim 1 wherein the enzyme or the cofactor is immobilized on a solid matrix having a planar surface and means are provided for substituting said matrix with another matrix.

3. The reactor according to claim 2 wherein the support matrix of the enzyme or cofactor is in the form of a film or a sheet or a membrane.

4. The reactor according to claim 1 wherein said matrix supporting the enzyme or the substrate is made of paper.

5. The reactor according to claim 1 wherein said channel is provided in both said first and second semi-blocks.

6. The reactor according to claim 1 wherein the reaction chamber consists of a continuous channel, the walls of the channel consisting of a lamina having a thickness between 0.1 and 0.2 mm, the closure of the reaction chamber being under pressure and being provided by the two semi-blocks having a planar surface urging against said lamina.

* * * * *